United States Patent
Neto et al.

(10) Patent No.: US 7,338,918 B2
(45) Date of Patent: Mar. 4, 2008

(54) CATALYST HAVING A SILVER-VANADIUM OXIDE PHASE AND A PROMOTER PHASE

(75) Inventors: Samuel Neto, Mannheim (DE); Frank Rosowski, Mannheim (DE); Sebastian Storck, Mannheim (DE); Stefan Bauer, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/594,128

(22) PCT Filed: Mar. 24, 2005

(86) PCT No.: PCT/EP2005/003179

§ 371 (c)(1),
(2), (4) Date: Sep. 25, 2006

(87) PCT Pub. No.: WO2005/092496

PCT Pub. Date: Oct. 6, 2005

(65) Prior Publication Data

US 2007/0213555 A1     Sep. 13, 2007

(30) Foreign Application Priority Data

Mar. 26, 2004  (DE) .................. 10 2004 014 918

(51) Int. Cl.
*B01J 23/50*  (2006.01)
*C07C 51/255* (2006.01)
*C07C 65/00*  (2006.01)
*C07C 45/00*  (2006.01)

(52) U.S. Cl. .............. 502/347; 562/415; 562/888; 568/431

(58) Field of Classification Search .................. None
See application file for complete search history.

(56) References Cited

U.S. PATENT DOCUMENTS 6,849,574 B1 *  2/2005  Heidemann et al. ........ 502/330

FOREIGN PATENT DOCUMENTS

| EP | 0 447 267 | 9/1991 |
|----|-----------|--------|
| WO | 99 62637  | 12/1999 |
| WO | 00 27753  | 5/2000 |
| WO | 01 85337  | 11/2001 |
| WO | 2005 012216 | 2/2005 |

* cited by examiner

*Primary Examiner*—Paul A. Zucker
(74) *Attorney, Agent, or Firm*—Oblon, Spivak, McClelland, Maier & Neustadt, P.C.

(57) ABSTRACT

A catalyst is described which has a catalytically active composition which contains a phase A and a phase B in the form of three-dimensional delimited regions, wherein phase A is a silver-vanadium oxide bronze and phase B a mixed oxide phase based on titanium dioxide and vanadium pentoxide. The catalyst serves to prepare aldehydes, carboxylic acids and/or carboxylic anhydrides from aromatic or heteroaromatic hydrocarbons by gas phase oxidation.

12 Claims, No Drawings

CATALYST HAVING A SILVER-VANADIUM OXIDE PHASE AND A PROMOTER PHASE

The present invention relates to a catalyst having a silver-vanadium oxide phase and a promoter phase and to a process for preparing aldehydes, carboxylic acids, and/or carboxylic anhydrides using the catalyst.

As is well known, a multitude of aldehydes, carboxylic acids and/or carboxylic anhydrides is prepared industrially by the catalytic gas phase oxidation of aromatic hydrocarbons such as benzene, o-, m- or p-xylene, naphthalene, toluene or durene (1,2,4,5-tetramethylbenzene) in fixed bed reactors, preferably tube bundle reactors. Depending on the starting material, for example, benzaldehyde, benzoic acid, maleic anhydride, phthalic anhydride, isophthalic acid, terephthalic acid or pyromellitic anhydride are obtained. To this end, a mixture of a molecular oxygen-containing gas, for example air and the starting material to be oxidized, is generally passed through tubes in which a bed of a catalyst is disposed.

WO 00/27753, WO 01/85337 and the patent application DE 10334132.3 having an earlier priority date than the present application describe multimetal oxides comprising silver oxide and vanadium oxide and their use for the partial oxidation of aromatic hydrocarbons.

It is an object of the invention to improve the yields achieved with these catalysts without impairing the selectivities.

According to the invention, this object is achieved by a catalyst comprising a catalytically active composition which contains a phase A and a phase B in the form of three-dimensional regions delimited from their local environment owing to their different chemical composition from their local environment, wherein phase A is a silver-vanadium oxide bronze and phase B a mixed oxide phase based on titanium dioxide and vanadium pentoxide.

The inventive catalysts are preferably coated catalysts, i.e. the catalytically active composition is applied to an inert support in the form of at least one shell.

In a preferred embodiment, phases A and B are distributed relative to one another as in a mixture of finely divided A and finely divided B. The particle sizes of the two phases are preferably in the range from 0.1 to 800 μm, in particular from 0.5 to 100 μm, more preferably from 1 to 100 μm.

In another preferred embodiment, phases A and B are arranged relative to one another as concentric shells. For this purpose, phase A (or a precursor therefor or sources of the elemental constituents thereof) is generally applied initially in coating form to an inert support and the thus coated support is then coated with phase B (or a precursor therefor or sources of the elemental constituents thereof). Although it is preferred that phase B fully covers phase A, partial covering with phase B is also conceivable.

The weight ratio of phase A to phase B is generally in the range from 80:20 to 98:2, preferably from 85:15 to 95:5.

The invention also relates to a process for preparing an above-defined catalyst, in which a powder which comprises phase A, a precursor therefor or sources of the elemental constituents thereof, and a powder B which comprises phase B, a precursor therefor or sources of the elemental constituents thereof are mixed and applied to an inert support.

The invention also relates to a process for preparing an above-defined catalyst, in which (i) phase A, a precursor therefor or sources of the elemental constituents thereof and (ii) phase B, a precursor therefor or sources of the elemental constituents thereof are applied successively to an inert support.

The invention also relates to a process for preparing aldehydes, carboxylic acids and/or carboxylic anhydrides, in which a gaseous stream which comprises an aromatic hydrocarbon and a molecular oxygen-containing gas are contacted at elevated temperature with an above-defined catalysts.

Silver-vanadium oxide bronzes and their preparation are known per se, for example from WO 00/27753 and WO 01/85337. These refer to silver-vanadium oxide compounds having an atomic Ag:V ratio of less than 1. These are generally semiconductive or metallically conductive, oxidic solids which preferably crystallize in layer or tunnel structures, and the vanadium in the $[V_2O_5]$ host lattice is partly reduced to V(IV). The catalytically active silver-vanadium oxide bronzes are formed above 200° C., in particular at temperatures of more than 300° C., by decomposition of certain multimetal oxides.

Phase A preferably has a composition which is obtainable by calcining a multimetal oxide of the general formula I

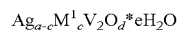

$$Ag_{a-c}M^1_c V_2 O_d * eH_2O \qquad \text{I}$$

where
a has a value from 0.3 to 1.9,
$M^1$ is at least one metal selected from alkali metals and alkaline earth metals, Bi, Tl, Cu, Zn, Cd, Pb, Cr, Au, Al, Fe, Co, Ni, Mo, Nb, Ce, W, Mn, Ta, Pd, Pt, Ru and/or Rh,
c is a value from 0 to 0.5, with the proviso that (a-c)≧0.1,
d is a number which is determined by the valency and frequency of the elements in the formula I other than oxygen, and
e has a value from 0 to 20, preferably from 0 to 5.

In the multimetal oxide of the formula I, the variable a preferably has a value of from 0.5 to 1.0 and more preferably from 0.6 to 0.9, the value of the variables b is preferably from 0 to 0.1, and the value of the variables c is preferably from 0.005 to 0.2, in particular from 0.01 to 0.1.

The number d is determined by the valency and frequency of the elements in the multimetal oxide of the formula I other than oxygen. The number e which is a measure of the water content is preferably from 0 to 5.

$M^1$ is preferably Na, K, Rb, Tl, Ni, W, Co, Fe, Mo, Nb, Zn, Ce and Mn.

Particular preference is given to multimetal oxides of the general formula Ia

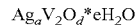

$$Ag_a V_2 O_d * eH_2O \qquad \text{Ia}$$

where
a has a value from 0.6 to 0.9,
d is as defined above, and
e has a value from 0 to 5.

The BET specific surface area, measured to DIN 66 131, which is based on the 1984 recommendations of the IUPAC, International Union of Pure and Applied Chemistry (see Pure & Appl. Chem. 57, 603 (1985)) is generally more than 1 m²/g, preferably from 3 to 250 m²/g, in particular from 10 to 250 m²/g and more preferably from 20 to 80 m²/g.

The multimetal oxide is preferably present in a crystal structure whose X-ray powder diffractogram is characterized by reflections at the interplanar spacings d 15.23±0.6, 12.16±0.4, 10.68±0.3, 3.41±0.04, 3.09±0.04, 3.02±0.04, 2.36±0.04 and 1.80±0.04 Å. In this application, the X-ray reflections are reported in the form of the interplanar spacings d[Å] which are independent of the wavelength of the X-radiation used and can be calculated from the reflection angle measured by means of the Bragg equation.

To prepare the multimetal oxides, a suspension of vanadium pentoxide ($V_2O_5$) is generally heated with the solution of a silver compound and also, if appropriate, a solution of a compound of the metal component M¹. Useful solvents for this reaction include polar organic solvents such as polyols, polyethers or amines, e.g. pyridine; the solvent used is preferably water. The silver salt used is preferably silver nitrate; the use of other soluble silver salts, e.g. silver acetate, silver perchlorate or silver fluoride, is likewise possible.

The salts of the metal component M¹ selected are generally those which are soluble in the solvent used. When water is used as the solvent in the preparation of the inventive multimetal oxides, it is possible to use, for example, the perchlorates or carboxylates, in particular the acetates, of the metal component M¹. Preference is given to using the nitrates of the metal component M¹ in question.

The reaction of the $V_2O_5$ with the silver compound and, if appropriate, the compound of the metal component M¹ may generally be carried out at room temperature or at elevated temperature. In general, the reaction is undertaken at temperatures of from 20 to 375° C., preferably from 20 to 100° C. and more preferably from 60 to 100° C. When the temperature of the reaction is above the temperature of the boiling point of the solvent used, the reaction is appropriately performed under the autogenous pressure of the reaction system in a pressure vessel. Preference is given to selecting the reaction conditions in such a way that the reaction can be carried out at atmospheric pressure. The duration of this reaction may, depending on the type of the starting materials converted and the temperature conditions employed, be from 10 minutes to 3 days. In the course of the reaction, the orange-red color of the $V_2O_5$ suspension changes and the new compound forms in the form of a dark brown suspension.

Depending upon the desired chemical composition of the multimetal oxide of the formula I, it is prepared by reacting together the amounts of $V_2O_5$, silver compound and the compound of the metal component M¹ which arise from a and c of formula I. On completion of reaction, the multimetal oxide is obtained with fibrous crystal morphology.

The thus formed metal oxide may be isolated from the reaction mixture and stored until further use. The isolation of the multimetal oxide may be effected, for example, by filtering off the suspension and drying the resulting solid, in which case the drying may be carried out in conventional dryers, but also, for example, in freeze dryers. The drying of the resulting multimetal oxide suspension is particularly advantageously carried out by means of spray drying. It may be advantageous to wash the multimetal oxide obtained in the reaction to free it of salts before it is dried. The spray drying is generally undertaken under atmospheric pressure or reduced pressure. The pressure employed and solvent used determine the inlet temperature of the drying gas—air is generally used as such, but it will be appreciated that other drying gases such as nitrogen or argon may also be utilized. The inlet temperature of the drying gas into the spray dryer is advantageously selected in such a way that the outlet temperature of the drying gas cooled by evaporation of the solvent does not exceed 200° C. for a prolonged period. In general, the outlet temperature of the drying gas is set to from 50 to 150° C., preferably from 100 to 140° C.

In addition to titanium dioxide (in the form of its anatase modification), phase B comprises vanadium pentoxide. In addition, small amounts of a multitude of other oxidic compounds may be present which, as promoters, influence the activity and selectivity of the catalyst. Phase B in the calcined state preferably contains from 1 to 20% by weight of vanadium oxide, calculated as $V_2O_5$, and from 80 to 99% by weight of titanium dioxide, calculated as $TiO_2$.

Examples of promoters include the alkali metal oxides such as cesium oxide, lithium oxide, potassium oxide and rubidium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxid, antimony oxide, cerium oxide and zinc oxide. In general, the promoter used from this group is cesium.

Useful additives which increase the activity but reduce the selectivity are in particular oxidic phosphorus compounds and ammonium hydrogenphosphate.

Phase B preferably has a composition of the formula II

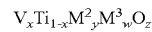

where
M² is at least one alkali metal;
M³ is an element of main group 5 of the Periodic Table of the Elements,
x has a value from 0.001 to 0.2,
y has a value from 0 to 0.01,
w has a value from 0 to 0.02, and
z is a number which is determined by the valency and frequency of the elements in the formula II other than oxygen.
M² is preferably Cs.
M³ is preferably Sb or P.

The components of the mixed oxide phase B are used in the form of their oxides or in the form of compounds which are converted to oxides on heating or on heating in the presence of oxygen. The vanadium component used may be vanadium oxides or vanadium compounds which are converted to vanadium oxide on heating, individually or in the form of mixtures thereof. Preference is given to using $V_2O_5$ or $NH_4VO_3$. It is also possible to use a reducing agent such as formic acid or oxalic acid in order to reduce the vanadium (V) compound at least partly to vanadium(IV). Suitable alkali metal compounds or compounds of the elements of main group 5 of the Periodic Table of the Elements are the corresponding oxides or compounds which are converted to oxides on heating, such as ammonium salts, sulfates, nitrates, carbonates. Suitable salts are, for example, $Na_2CO_3$, $K_2O$, $Cs_2O$, $Cs_2CO_3$, $Cs_2SO_4$, $P_2O_5$, $(NH_4)_2HPO_4$, $Sb_2O_3$.

To form phase B, an aqueous slurry of the compound of the vanadium component, of titanium dioxide and of M² in suitable amounts is generally prepared and the slurry is stirred until sufficient homogenization has been achieved. The slurry may then be spray-dried or be used as such for coating.

The inventive catalysts are appropriately prepared via the stage of a "precatalyst" which can be stored and handled as such, and from which the active catalyst can either be prepared by thermal treatment or obtained in situ in an oxidation reactor under the conditions of the oxidation reaction. In the course of the thermal treatment of the precatalysts at temperatures of from above 200 to 650° C., preferably at from above 250 to 500° C., in particular at from 300 to 450° C., the multimetal oxides present in the precatalyst decompose to silver-vanadium oxide bronzes which form phase A of the inventive catalyst. This conversion of the inventive multimetal oxides present in the precatalyst to silver-vanadium oxide bronzes also takes place in particular in situ in the reactor for the gas phase partial oxidation of aromatic hydrocarbons, when the precatalyst is used in this reaction. The resulting silver-vanadium oxide bronzes are the catalytically active constituents of the catalytically active layer of the inventive coated catalyst. The thermal conversion of the multimetal oxides to silver-vanadium oxide bronzes proceeds via a series of reduction and oxidation reactions which individually have not yet been understood.

The inert nonporous support material for the inventive catalysts may be virtually any prior art support materials, as advantageously find use in the preparation of coated catalysts for the oxidation of aromatic hydrocarbons to aldehydes, carboxylic acids and/or carboxylic anhydrides, for example quartz ($SiO_2$), porcelain, magnesium oxide, tin oxide, silicon carbide, rutile, clay earth ($Al_2O_3$), aluminum silicate, steatite (magnesium silicate), zirconium silicate, cerium silicate or mixtures of these support materials. The term "nonporous" is to be understood in the sense of "nonporous apart from industrially ineffective numbers of pores", since it is industrially unavoidable that a small number of pores might be present in the support material which ideally should not contain any pores. Advantageous support materials which should be emphasized are in particular steatite and silicon carbide. The form of the support material is generally not critical for the inventive precatalysts and coated catalysts. For example, catalyst supports can be used in the form of spheres, rings, tablets, spirals, tubes, extrudates or spall. The dimensions of these catalyst supports correspond to those of catalyst supports typically used to prepare coated catalysts for the gas phase partial oxidation of aromatic hydrocarbons.

For the shell-type coating of the inert support material, known processes are used. For example, a suspension of the active composition or of a precursor may be sprayed onto the catalyst support in a heated coating drum at elevated temperature. Instead of coating drums, fluidized bed coaters may also be used.

The suspension medium is generally water to which have preferably been added binders such as higher alcohols, polyhydric alcohols, e.g. ethylene glycol, 1,4-butanediol or glycerol, dimethylformamide, dimethylacetamide, dimethyl sulfoxide, N-methylpyrrolidone or cyclic ureas such as N,N'-dimethylethyleneurea or N,N'-dimethylpropyleneurea, or (co)polymers, dissolved or advantageously in the form of an aqueous dispersion, and suitable binder contents are generally from 10 to 20% by weight, based on the solids content of the suspension. Suitable polymeric binders are, for example, vinyl acetate/vinyl laurate, vinyl acetate/acrylate, styrene/acrylate, vinyl acetate/maleate or vinyl acetate/ethylene copolymers. In a thermal treatment at temperatures from above 200 to 500° C., the binder escapes by thermal decomposition and/or combustion from the applied layer.

In order to obtain catalysts in whose active composition phases A and B are distributed relative to one another as in a mixture of finely divided A and finely divided B, it is appropriate to mix the powder, obtained after isolation and drying, of the above-mentioned multimetal oxide with a powder which comprises the elemental constituents of the mixed oxide phase B, and apply the mixture to the inert support in the manner described.

The layer thickness of the catalyst coating or the sum of the layer thicknesses of the coatings which comprise the catalystically active constituents is generally from 10 to 250 µm.

The inventive catalysts are used for the partial oxidation of aromatic or heteroaromatic hydrocarbons to aldehydes, carboxylic acids and/or carboxylic anhydrides, in particular for the gas phase partial oxidation of o-xylene and/or naphthalene to phthalic anhydride, of toluene to benzoic acid and/or benzaldehyde, or of methylpyridines such as α-picoline to pyridinecarboxylic acids such as nicotinic acid, with a molecular oxygen-containing gas. The inventive catalysts may be used for this purpose alone or in combination with other catalysts having different activity, for example prior art catalysts based on vanadium oxide/anatase, in which case the different catalysts are generally disposed in the reactor in separate catalyst beds which may be disposed in one or more fixed catalyst beds.

For this purpose, the inventive coated catalysts or precatalysts are charged into the reaction tubes of a tubular reactor which is thermostated to the reaction temperature externally, for example by means of a salt melt. When an above-defined precatalyst is used instead of the inventive coated catalyst, this forms an inventive coated catalyst under the temperature conditions of the partial oxidation. The reaction gas is passed over the thus prepared catalyst bed at temperatures of from 100 to 650° C. and preferably from 250 to 480° C., and at an elevated pressure of generally from 0.1 to 2.5 bar, preferably from 0.3 to 1.5 bar, with a superficial velocity of generally from 750 to 5000 $h^{-1}$.

The reaction gas supplied to the catalyst is generally obtained by mixing a molecular oxygen-containing gas, which, apart from oxygen, may also contain suitable reaction moderators and/or diluents such as steam, carbon dioxide and/or nitrogen, with the aromatic hydrocarbon to be oxidized, and the molecular oxygen-containing gas may generally contain from 1 to 100% by volume, preferably from 2 to 50% by volume and more preferably from 10 to 30% by volume, of oxygen, from 0 to 30% by volume, preferably from 0 to 20% by volume, of steam, and from 0 to 50% by volume, preferably from 0 to 1% by volume, of carbon dioxide, remainder nitrogen. To obtain the reaction gas, the molecular oxygen-containing gas is generally charged with from 30 to 300 g per $m^3$ (STP), preferably with from 70 to 150 g per $m^3$ (STP) of gas, of the aromatic hydrocarbon to be oxidized. The molecular oxygen-containing gas used is particularly advantageously air.

Advantageously, the gas phase partial oxidation is carried out in such a way that two or more zones, preferably two zones, of the catalyst bed disposed in the reaction tube are thermostated to different reaction temperatures, for which, for example, reactors having separate salt baths may be used. When the reaction is carried out in two reaction zones, the reaction zone located toward the gas inlet of the reaction gas, which generally includes from 30 to 80% by volume of the entire catalyst volume, is thermostated to a reaction temperature from 1 to 20° C. higher, preferably from 1 to 10° C. higher and in particular from 2 to 8° C. higher than the reaction zone located toward the gas outlet. Such a procedure is referred to as two-zone or multizone structuring of the reactor. Alternatively, the gas phase oxidation may also be carried out without division into temperature zones at a uniform reaction temperature.

In a preferred embodiment of the process for partially oxidizing aromatic hydrocarbons and heterocycles (e.g. methylpyridine or β-picoline) to aldehydes, carboxylic acids and/or carboxylic anhydrides, which is found to be particularly advantageous for the preparation of phthalic anhydride from o-xylene and/or naphthalene, the aromatic hydrocarbon is initially converted to a reaction mixture over a bed of the inventive catalyst with partial conversion. The resulting reaction mixture or a fraction thereof may then be contacted with at least one further catalyst whose catalytically active composition comprises vanadium pentoxide and anatase.

In the case of the preparation of phthalic anhydride from o-xylene, the semiconverted reaction mixture comprises, for example, phthalic anhydride and other oxidation products such as o-tolualdehyde, o-toluenecarboxylic acid and phthalide, and unconverted o-xylene. It may then be further processed by either a) removing the o-xylene from the phthalic anhydride and the other oxidation products which are intermediates on the reaction path from o-xylene to phthalic anhydride and recycling it, and feeding the stream composed of phthalic anhydride and intermediates to one or more further catalyst beds having, for example, a coated catalyst based on vanadium oxide/anatase, where the intermediates are o-xidized selectively to phthalic anhydride; or by b) passing the product mixture without further workup, i.e. without o-xylene removal, over a second or, if appropriate, over further catalyst beds.

Preference is given to passing the gaseous stream successively over a bed of a catalyst disposed downstream and a bed of a catalyst disposed upstream, the bed of the catalyst disposed upstream comprising an inventive catalyst and the bed of the catalyst disposed downstream comprising at least one catalyst whose catalytically active composition comprises vanadium pentoxide and anatase. In general, the catalytically active composition of the catalyst disposed downstream contains from 1 to 40% by weight of vanadium oxide, calculated as $V_2O_5$, from 60 to 99% by weight of titanium dioxide, calculated as $TiO_2$, up to 1% by weight of a cesium compound, calculated as Cs, up to 1% by weight of a phosphorus compound, calculated as P, and up to 10% by weight of antimony oxide, calculated as $Sb_2O_3$. Advantageously, the bed of the catalyst disposed downstream comprises at least two layers of catalysts whose catalytically active composition has a different Cs content, the Cs content falling in the flow direction of the gaseous stream.

This type of reaction control achieves overall a distinctly higher phthalic anhydride yield than when catalyst systems based on vanadium oxide/anatase are used alone, since the inventive catalysts can oxidize o-xylene and or naphthalene substantially more selectively to phthalic anhydride or the aforementioned intermediates.

It is possible to proceed in a similar manner in the oxidation of toluene to benzaldehyde and/or benzoic acid or the oxidation of β-picoline to nicotinic acid. Benzaldehyde finds use, for example, as an aroma. Nicotinic acid finds use, for example, as a starting material for the preparation of vitamins.

EXAMPLES

Catalysts

A Preparation of the Multimetal Oxide $Ag_{0.73}V_2O_x$ 102 g of $V_2O_5$ (=0.56 mol) were added with stirring to 7 l of demineralized water at 60° C. An aqueous solution of 69.5 g of $AgNO_3$ (=0.409 mol) in 1 l of water was added with further stirring to the resulting orange-colored suspension. Subsequently, the temperature of the resulting suspension was increased to 90° C. within 2 hours and the mixture was stirred at this temperature for 24 hours. Afterward, the resulting dark brown suspension was cooled and spray-dried (inlet temperature (air)=350° C., outlet temperature (air)=110° C.).

The resulting powder had a BET specific surface area of 56 $m^2/g$. With the aid of a Siemens D 5000 diffractometer using Cu—Kα radiation (40 kV, 30 mA), a powder X-ray diffractogram of the resulting powder was recorded. The diffractometer was equipped with an automatic primary and secondary diaphragm system and also a secondary monochromator and scintillation detector. From the powder X-ray diffractogram, the following interplanar spacings d [Å] were obtained with the accompanying relative intensities $I_{rel}$ [%]: 15.04 (11.9), 11.99 (8.5), 10.66 (15.1), 5.05 (12.5), 4.35 (23), 3.85 (16.9), 3.41 (62.6), 3.09 (55.1), 3.02 (100), 2.58 (23.8), 2.48 (27.7), 2.42(25.1), 236 (34.2), 2.04 (26.4), 1.93 (33.2), 1.80 (35.1), 1.55 (37.8).

B1 Preparation of a $V_2O_5/TiO_2$ Phase with 0.4% by Weight Cs 13.0 g of oxalic acid dihydrate (=0.12 mol) and then 3.35 g of $V_2O_5$ (=0.17 mol) were added with stirring to 100 ml of demineralized water at 60° C. The resulting blue solution was heated to 90° C. with further stirring for 30 min. After cooling to room temperature, 0.46 g of cesium sulfate (=0.0013 mol), 38.9 g of formamide, 80 g of anatase having a BET surface of 21 $m^2/g$ and 157.5 g of water were added (solids content about 21%). Subsequently, the resulting suspension was stirred at 25° C. for 15 hours. The suspension was then spray-dried (inlet temperature (air)=350° C.; outlet temperature (air)=110° C.). The spray powder consisted on average of 4.0% by weight vanadium (calculated as $V_2O_5$), 0.40% by weight cesium (calculated as Cs) and 95.6% by weight titanium dioxide.

B2 Preparation of a $V_2O_5/TiO_2$ Phase with 0.5% by Weight Cs 13.0 g of oxalic acid dihydrate (=0.12 mol) and then 3.35 g of $V_2O_5$ (=0.17 mol) were added with stirring to 100 ml of demineralized water at 60° C. The resulting blue solution was heated to 90° C. with further stirring for 30 min. After cooling to room temperature, 0.58 g of cesium sulfate (=0.0016 mol), 38.9 g of formamide, 80 g of anatase having a BET surface of 21 $m^2/g$ and 157.4 g of water were added (solids contenting a BET surface of 21 $m^2/g$ and 157.4 g of water were added (solids content about 21%). Subsequently, the resulting suspension was stirred at 25° C. for 15 hours. The suspension was then spray-dried (inlet temperature (air)=350° C.; outlet temperature (air)=110° C.). The spray powder consisted on average of 4.0% by weight vanadium (calculated as $V_2O_5$), 0.50% by weight cesium (calculated as Cs) and 95.6% by weight titanium dioxide.

Catalyst Preparation

Application of the Phases as a Powder Mixture to Spheres

To prepare catalysts 1 to 7, powder A was mixed with from 0 to 20% by weight of powder B1 or B2 (see table) and applied to magnesium silicate spheres as follows: 300 g of steatite spheres having a diameter of from 3.5 to 4 mm were coated in a coating drum at 20° C. over 20 min with 40 g of the mixed powder and 4.4 g of oxalic acid with the addition of 35.3 g of a mixture containing 60% by weight water and 40% by weight glycerol, and subsequenty dried. The weight of the thus applied catalytically active composition, determined on a sample of the precatalyst obtained, after heat treatment at 400° C. for 1 hour, was 10% by weight based on the total weight of the finished catalyst.

Application of the Phases in the Form of Concentric Shells to Spheres

To prepare catalyst 8, the powders A and B1 were applied as follows to magnesium silicate spheres: 300 g of steatite spheres having a diameter of from 3.5 to 4 mm were coated in a coating drum at 20° C. over 20 min with 36 g of powder A and 4 g of oxalic acid. The coated spheres were then coated with 6 g of powder B1 with the addition of 30 g of a mixture containing 60% by weight water and 40% by weight glycerol, and subsequently dried. The weight of the thus applied catalytically active composition, determined on a sample of the resulting precatalyst, after heat treatment at 400° C. for 1 hour, was 10% by weight based on the total weight of the finished catalyst, of which 86% by weight were accounted for by the inner layer of the silver-vanadium oxide bronze and 14% by weight by the outer layer of the $V_2O_5/TiO_2$ phase.

Application of the Phases as a Powder Mixture to Rings

For use examples 2 to 4, powder A was mixed with from 0 to 10 weight of powder B1 and applied to magnesium silicate rings as follows: 350 g of steatite rings having an external diameter of 7 mm, a length of 3 mm and a wall thickness of 1.5 mm were coated in a coating drum at 20° C. over 20 min with 84.4 g of the mixed powder and 9.4 g of oxalic acid with the addition of 66.7 g of a mixture containing 60% by weight water and 40% by weight glycerol, and subsequently dried. The weight the thus applied catalytically active composition, determined on a sample of the resulting precatalyst, after treatment at 450° C. for 1 hour, was 18% by weight based on the total weight of the finished catalyst.

Reference Catalyst 1 ($V_2O_5/TiO_2$)

1400 g of steatite (magnesium silicate) rings having an external diameter of 8 mm, a length of 6 mm and a wall thickness of 1.6 mm were heated to 160° C. in a coating drum and, together with 13.8 g of an organic binder consisting of a copolymer of acrylic acid/maleic acid (weight ratio 75:25), sprayed with a suspension of 466 g of anatase having a BET surface area of 21 $m^2/g$, 67.2 g of vanadyl oxalate, 14.4 g of antimony trioxide, 3.15 g of ammonium hydrogenphosphate, 2.87 g of cesium sulfate, 721 g of water and 149 g of formamide. The catalytically active composition applied in this way consisted on average of 0.16% by weight phosphorus (calculated as P), 7.5% by weight vanadium (calculated as $V_2O_5$), 3.2% by weight antimony (calculated as $Sb_2O_3$), 0.40% by weight cesium (calculated as Cs) and 88.74% by weight titanium dioxide.

The thus obtained coated catalyst was heated to 160° C. in a coating drum and, together with 14 g of an organic binder consisting of a copolymer of acrylic acid/maleic acid (weight ratio 75:25), sprayed with a suspension of 502 g of anatase having a BET surface area of 21 $m^2/g$, 35.8 g of vanadyl oxalate, 2.87 g of cesium sulfate, 720 g of water and 198 g of formamide. The catalytically active composition applied in this way consisted on average of 4.0% by weight vanadium (calculated as $V_2O_5$), 0.4% by weight cesium (calculated as Cs) and 88.8% by weight titanium dioxide. The weight of the applied layers was 9.3% by weight of the total weight of the finished catalyst.

Reference Catalyst 2 ($V_2O_5/TiO_2$ Catalyst)

1400 g of steatite (magnesium silicate) rings having an external diameter of 8 mm, a length of 6 mm and a wall thickness of 1.6 mm were heated to 160° C. in a coating drum and sprayed with a suspension of 468 g of anatase having a BET surface area of 21 $m^2/g$, 67.2 g of vanadyl oxalate, 16.8 g of antimony trioxide, 2.95 g of ammonium hydrogenphosphate, 0.72 g of cesium sulfate, 719 g of water and 150 g of formamide, until the weight of the applied layer was 10.5% of the total weight of the finished catalyst (after heat treatment at 450° C. for 1 hour). The catalytically active composition applied in this way, i.e. the catalyst coating, consisted on average of 0.15% by weight phosphorus (calculated as P), 7.5% by weight vanadium (calculated as $V_2O_5$), 3.2% by weight antimony (calculated as $Sb_2O_3$), 0.1% by weight cesium (calculated as Cs) and 89.05% by weight titanium dioxide.

Use Examples

1. Preparation of Phthalic Anhydride

An 80 cm-long iron tube having an internal width of 16 mm was charged with the catalysts according to the table (coated steatite spheres) up to a bed length of 66 cm. For temperature control, the iron tube was surrounded by an electrical heating mantle. In the experiments, the temperature is 350° C. Every hour, 360 l (STP) of air laden with 98.5% by weight o-xylene was passed through the tube at a loading of 60 g of xylene/$m^3$ (STP) of air. The table which follows summarizes the results obtained.

TABLE

| Catalyst | $Ag_{0.73}V_2O_x$ phase A | $V_2O_5/TiO_2$ phase B1 | B2 | Conversion (mol %) | $CO_x$ selectivity[1] (mol %) |
|---|---|---|---|---|---|
| 1 | — | 100% | — | 81 | 33 |
| 2 | 100% | — | — | 37 | 10 |
| 3 | 98% | 2% | — | 49 | 16 |
| 4 | 95% | 5% | — | 44 | 11 |
| 5 | 90% | 10% | — | 42 | 12 |
| 6 | 80% | 20% | — | 35 | 12 |
| 7 | 90% | — | 10% | 44 | 9 |
| 8 | 86%[2] | 14%[2] | — | 49 | 9 |

[1]"$CO_x$ selectivity" corresponds to the proportion of the o-xylene converted to combustion products (CO, $CO_2$); the residual selectivity to 100% corresponds to the proportion of the o-xylene converted to the product of value, phthalic anhydride, and the intermediates, o-tolualdehyd, o-toluic acid and phthalide, and also by-products such as maleic anhydride, citraconic anhydride and benzoic acid
[2]concentrically applied shells A deinstalled sample of catalyst 2 (having 100% phase A) was used to determine a BET surface area of the active composition of 6.7 $m^2/g$ and a vanadium oxidation stage of 4.63. From the powder X-ray diffractogram, the following interplaner spacings d [Å] with the accompanying relative itensities $I_{rel}$[%] were obtained: 4.85 (9.8), 3.50 (14.8), 3.25 (39.9), 2.93 (100), 2.78 (36.2). 2.55 (35.3), 2.43 (18.6), 1.97 (15.2), 1.95 (28.1), 1.86 (16.5), 1.83 (37.5), 1.52 (23.5). The deinstalled samples of catalysts 3-7 exhibited no changes in the Ag/V phase relating to powder X-ray diffactogram, BET surface area (about 6.7 $m^2/g$) and vanadium oxidation state (4.67).

2. Preparation of Phthalic Anhydride (Comparative Example)

A 3.85 m long irong tube having an internal width of 25 mm was charged from bottom to top with in each case 0.80 m of reference catalyst 2, 1.40 m of reference catalyst 1 and subsequently 0.80 m of a catalyst (coated steatite rings) whose active composition consisted of 100% by weight A. For temperature control, the iron tube was surrounded by a salt melt. Every hour, 4.0 $m^3$ (STP) of air laden with 98.5% by weight o-xylene was passed through the tube at a loading of 80 g of xylene/$m^3$ (STP) of air were passed through the tube from top to bottom. At a salt bath temperature of from 353 to 360° C., an average PA yield of 115.5% by weight was achieved (yield means the phthalic anhydride obtained in percent by weight based on 100% o-xylene). The conversion was more than 99.94%, the residual phthalide content at the reactor outlet was less than 0.35% by weight.

3. Preparation of Phthalic Anhydride

Use example 2 was repeated, except that in each case 1.00 m of reference catalyst 2, 1.60 m of reference catalyst 1 and subsequently 0.40 m of a catalyst (coated steatite rings) whose active composition was composed of 90% by weight A and 10% by weight B1 were charged. An average PA yield of 116.4% by weight was achieved. The conversion was more than 99.94%, the residual phthalide content at the reactor outlet was less than 0.30% by weight. This example shows that, when the inventive catalysts are used, high PA yields can be achieved even with a distinctly shortened bed length of the silver-vanadium oxide catalyst compared to use example 2.

4. Preparation of Phthalic Anhydride

Use example 2 was repeated, except that in each case 0.80 m of reference catalyst 2, 1.80 m of reference catalyst 1 and subsequently 0.40 m of a catalyst (coated steatite rings) whose active composition was composed of 90% by weight A and 10% by weight B1 were charged. An average PA yield of 116.9% by weight was achieved. The conversion was more than 99.94%, the residual phthalide content at the reactor outlet was less than 0.35% by weight. This example shows that, when the inventive catalysts are used, high PA yields can be achieved even with an adapted bed length distribution of the reference catalysts compared to use example 2.

What is claimed is:

1. A catalyst comprising a catalytically active composition which contains a phase A and a phase B in the form of three-dimensional regions delimited from their local environment owing to their different chemical composition from their local environment, wherein phase A is a silver-vanadium oxide bronze and phase B a mixed oxide phase based on titanium dioxide and vanadium pentoxide.

2. The catalyst according to claim 1, wherein the catalytically active composition is applied to an inert support.

3. The catalyst according to claim 2, wherein phases A and B are distributed relative to one another as in a mixture of finely divided A and finely divided B.

4. The catalyst according to claim 2, wherein phases A and B are arranged relative to one another as concentric shells.

5. The catalyst according to claim 1, wherein the weight ratio of phase A to phase B is in the range from 85:15 to 95:5.

6. The catalyst according to claim 1, wherein phase A has a composition obtained by calcining a multimetal oxide of general formula I $$Ag_{a-c}M^1{}_cV_2O_d \cdot eH_2O \qquad I$$

wherein

M$^1$ is at least one metal selected from alkali metals and alkaline earth metals, Bi, Tl, Cu, Zn, Cd, Pb, Cr, Au, Al, Fe, Co, Ni, Mo, Nb, Ce, W, Mn, Ta, Pd, Pt, Ru and/or Rh, a has a value from 0.3 to 1.9, c is a value from 0 to 0.5, with the proviso that (a−c)≧0.1, d is a number which is determined by the valency and frequency of the elements in formula I other than oxygen, and e has a value from 0 to 20.

7. The catalyst according to claim 1, wherein phase B has a composition of formula II $$V_xTi_{1-x}M^2{}_yM^3{}_wO_z \qquad II$$

wherein

M$_2$ is at least one alkali metal,

M$_3$ is an element of main group 5 of the Periodic Table of the Elements, x has a value from 0.001 to 0.2, y has a value from 0 to 0.01, w has a value from 0 to 0.02, and z is a number which is determined by the valency and frequency of the elements in formula II other than oxygen.

8. A process for preparing the catalyst according to claim 3, in which a powder which comprises phase A, a precursor therefor or sources of the elemental constituents thereof, and a powder which comprises phase B, a precursor therefor or sources of the elemental constituents thereof are mixed and applied to said inert support.

9. A process for preparing the catalyst according to claim 4, in which (i) phase A, a precursor therefor or sources of the elemental constituents thereof and (ii) phase B, a precursor therefor or sources of the elemental constituents thereof are applied successively to said inert support.

10. A process for preparing aldehydes, carboxylic acids and/or carboxylic anhydrides, in which a gaseous stream which comprises an aromatic or heteroaromatic hydrocarbon and a molecular oxygen-containing gas are contacted at elevated temperature with the catalyst according to claim 1.

11. The process according to claim 10, in which the gaseous stream is passed successively over a bed of a catalyst disposed downstream and a bed of a catalyst disposed upstream, the bed of the catalyst disposed upstream containing a catalyst composition which contains a phase A and a phase B in the form of three-dimensional regions delimited from their local environments owing to their different chemical composition from their local environment, wherein phase A is a silver-vanadium oxide bronze and phase B is a mixed oxide phase based on titanium dioxide and vanadium pentoxide and the bed of the catalyst disposed upstream containing at least one catalyst whose catalytically active composition consists of a mixed oxide phase based on titanium dioxide and vanadium pentoxide.

12. The process according to claim 10, in which the aromatic hydrocarbon oxidized is o-xylene or naphthalene or a mixture of o-xylene and naphthalene to give phthalic anhydride.

* * * * *